United States Patent
Hummelshøj

(10) Patent No.: US 10,428,804 B2
(45) Date of Patent: Oct. 1, 2019

(54) PROTEIN ARRAY FOR CONVERTING CHEMICAL ENERGY INTO MECHANICAL ENERGY

(71) Applicant: Toyota Research Institute, Inc., Los Altos, CA (US)

(72) Inventor: Jens Strabo Hummelshøj, Burlingame, CA (US)

(73) Assignee: Toyota Research Institute, Inc., Los Altos, CA (US)

( * ) Notice: Subject to any disclaimer, the term of this patent is extended or adjusted under 35 U.S.C. 154(b) by 0 days.

(21) Appl. No.: 15/803,041

(22) Filed: Nov. 3, 2017

(65) Prior Publication Data

US 2019/0136838 A1 May 9, 2019

(51) Int. Cl.
*F03G 7/00* (2006.01)
*C25B 9/18* (2006.01)
*C25B 13/08* (2006.01)
*C07K 14/00* (2006.01)

(52) U.S. Cl.
CPC .............. *F03G 7/005* (2013.01); *C07K 14/00* (2013.01); *C25B 9/18* (2013.01); *C25B 13/08* (2013.01)

(58) Field of Classification Search
CPC ...................................... F03G 7/005; C07K 14/00; C25B 9/18; C25B 13/08
See application file for complete search history.

(56) References Cited

U.S. PATENT DOCUMENTS

| 5,226,292 A | 7/1993 | Urry |
| 9,651,548 B2 | 5/2017 | Aizenberg et al. |
| 2003/0138777 A1* | 7/2003 | Evans ............ B82Y 5/00 435/6.18 |

FOREIGN PATENT DOCUMENTS

JP H0886272 A 4/1996

OTHER PUBLICATIONS

Chin, "Electrochemical to Mechanical Energy Conversion", Massachusetts Institute of Technology, 2010, 153 pages.
Xue et al., "Hybridizing Energy Conversion and Storage in a Mechanical-to-Electrochemical Process for Self-Charging Power Cell", American Chemical Society, 2012, 7 pages.
Hill et al., "Subunit treadmilling of microtubules or actin in the presence of cellular barriers: Possible conversion of chemical free energy into mechanical work", National Academy of Sciences, Jan. 1982, 6 pages.

(Continued)

*Primary Examiner* — Arun S Phasge
(74) *Attorney, Agent, or Firm* — Christopher G. Darrow; Darrow Mustafa PC

(57) ABSTRACT

Systems, methods and devices for direct conversion of chemical energy into mechanical energy are provided. The system can have a flow of ions, such as between an anode and a cathode. In between the flow of ions, is a membrane, either synthetic or biologically derived. Proteins are bound to that membrane. Further, the proteins are responsive to the ions and undergo a conformational shift, thus using the presence or absence of ions for creating movement. This portion can be referred to as a "kinetic cell". A portion of the proteins, such as the aqueous portion, can be tethered to a moveable substrate, which translates the motion in the kinetic cell to the exterior. Multiple kinetic cells can be used in coordination to increase the kinetic force generated, analogous to a battery stack.

20 Claims, 7 Drawing Sheets

(56) References Cited

OTHER PUBLICATIONS

Kuhn, "Size and Shape Changes of Polyelectrolytes: Conversion of Chemical Into Mechanical Energy", Nature, Sep. 20, 1958, 3 pages.
Osada et al., "Conversion of chemical into mechanical energy by contractile polymers performed by polymer complexion", Polymer, 5 pages.
Schneider et al., "Supramolecular Interactions in Chemomechanical Polymers", ACCOUNTS of chemical research, 12 pages.
Osada, "Conversion of Chemical Into Mechanical Energy by Synthetic Polymers (Chemomechanical Systems)", Advances in Polymer Science 82, 1987 (46 pages).

* cited by examiner

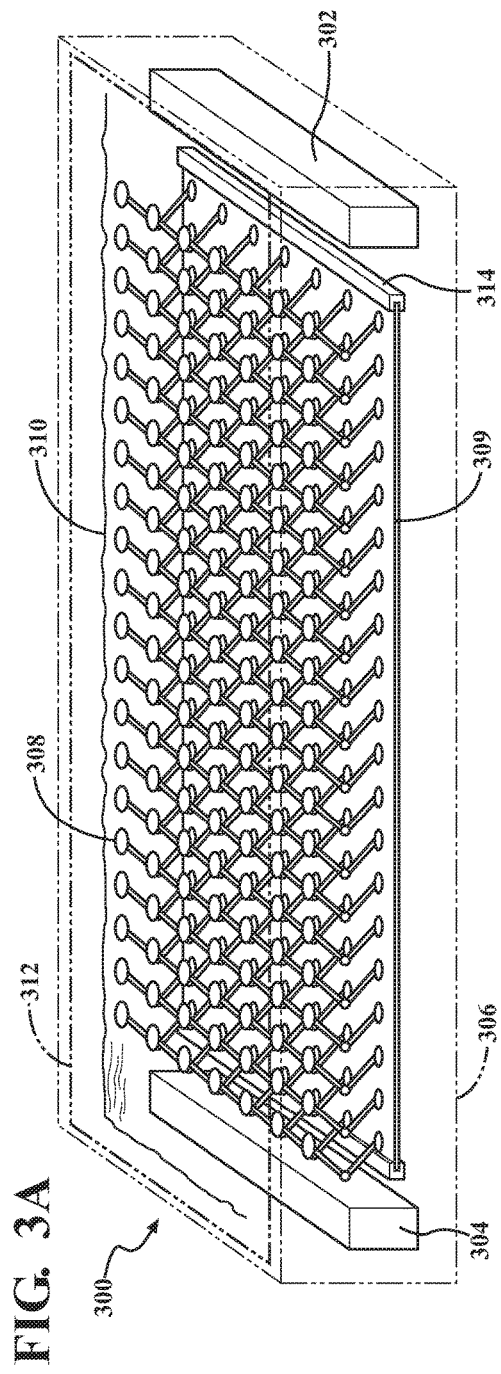
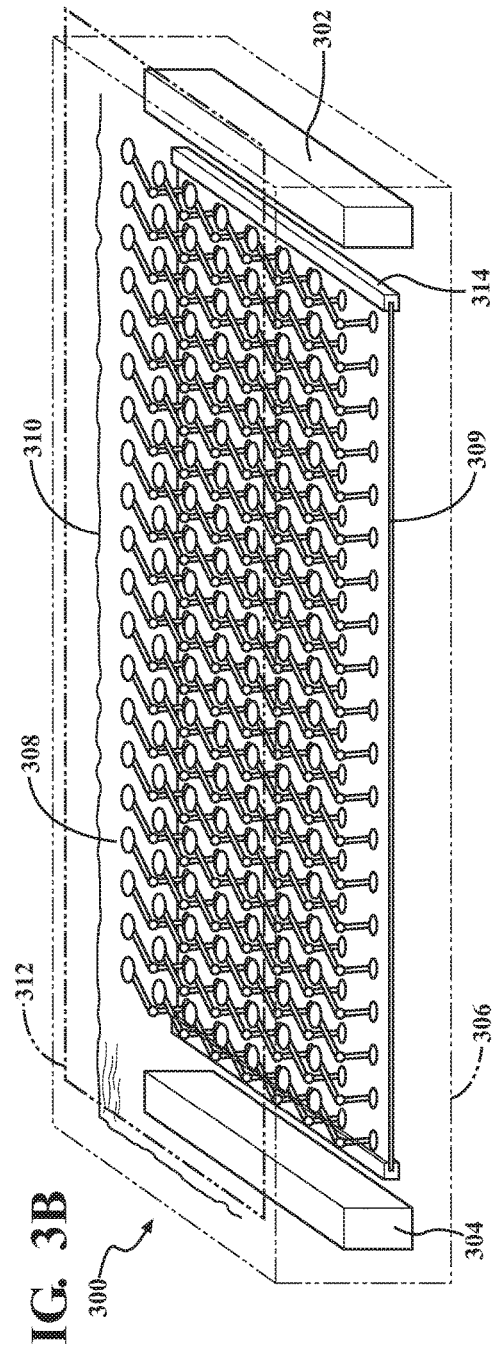

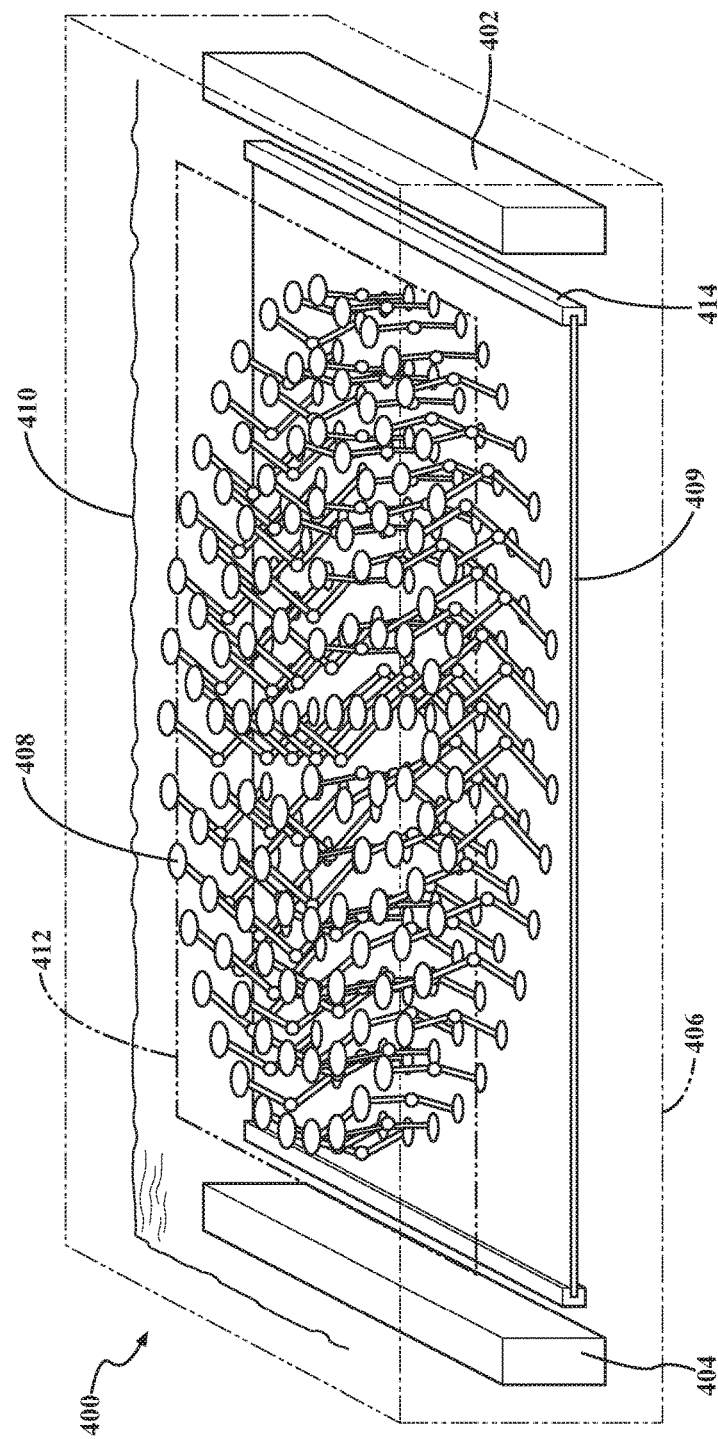

PROTEIN ARRAY FOR CONVERTING CHEMICAL ENERGY INTO MECHANICAL ENERGY

TECHNICAL FIELD

The present invention generally relates to the conversion of chemical energy to mechanical energy and, more specifically, to mechanical systems involving ion-responsive proteins or polymers.

BACKGROUND

The chemical-electrical-mechanical conversion process is the process by which chemical energy is used to create electrical energy, which can then be used to create mechanical energy. Batteries, such as lithium-ion batteries, generally include a positive current collector (e.g., aluminum such as an aluminum foil) having an active material provided thereon (e.g., LiCoO2) and a negative current collector (e.g., copper such as a copper foil) having an active material (e.g., a carbonaceous material such as graphite) provided thereon. The chemical reaction that ensues in a battery is used to produce electricity for connected devices, such as an electric motor, where the electrical energy can be converted to mechanical energy.

However, the chemical-electrical-mechanical conversion creates significant energy loss. In the case of lithium-ion batteries, conversion efficiency from chemical to electrical is no more than about 80-90%. As coupled to a low watt motor (less than 10 W), the conversion efficiency is between 30-60%, create an overall chemical-electrical-mechanical conversion efficiency of between 24-54%. This means there is a cumulative energy waste for each step in the conversion process. As such, though chemical energy is one of the most efficient means currently available to store energy, much of this stored energy is still lost in the conversion to mechanical work.

SUMMARY

The devices, systems and methods described herein use proteins or polymers responsive to differences in ion concentration to convert chemical energy directly to mechanical work. In one embodiment, a kinetic cell is described. The kinetic cell can include a chamber. The kinetic cell can further include a donor source comprising a target ion, the donor source in a first position in the chamber. The kinetic cell can further include a recipient source in a second position in the chamber. The kinetic cell can further include a membrane positioned in the chamber between the donor source and the recipient source. The kinetic cell can further include an array of proteins comprising a plurality of ion-responsive proteins, each ion-responsive protein having a first connecting region and a second connecting region, the ion-responsive protein being attached to the membrane at the second connecting region. The kinetic cell can further include an ion-containing solution in the chamber and in fluid communication with the donor source, the recipient source, and the array of proteins. The kinetic cell can further include a support structure attached to at least a portion of the array of proteins at the first connecting region.

In another embodiment, a chemomechanical system for converting chemical energy to mechanical movement is disclosed. The chemomechanical system can include one or more kinetic cells; and a mechanical energy transmission device connected with the one or more kinetic cells. Each of the one or more kinetic cells can include a chamber. Each of the one or more kinetic cells can further include a donor source comprising a target ion, the donor source in a first position in the chamber. Each of the one or more kinetic cells can further include a recipient source in a second position in the chamber. Each of the one or more kinetic cells can further include a membrane positioned in the chamber between the donor source and the recipient source. Each of the one or more kinetic cells can further include an array of proteins comprising a plurality of ion-responsive proteins, each ion-responsive protein having a first connecting region and a second connecting region, the ion-responsive protein being attached to the membrane at the second connecting region. Each of the one or more kinetic cells can further include an ion-containing solution in the chamber and in fluid communication with the donor source, the recipient source, and the array of proteins. Each of the one or more kinetic cells can further include and a support structure attached to at least a portion of the array of proteins at the first connecting region, wherein the one or more kinetic cells configured to produce a movement. The mechanical energy transmission device can include a connection end forming a connection with at least a portion of the support structure, the connection end configured to receive the movement from the one or more kinetic cells. The mechanical energy transmission device can further include a force conversion device connected with the connection end, the force conversion device configured to receive movement from the connection end, convert said movement to a first force, and apply said first force to perform mechanical work.

In another embodiment, a method for converting chemical energy to mechanical energy is disclosed. The method can include attaching an array of ion-responsive microstructures to a first support structure and a second support structure. The method can further include delivering a plurality of ions to the array of ion-responsive microstructures, the plurality of ions causing a conformational shift in the ion-responsive microstructures. The method can further include directing the conformational shift to create a movement in the second support structure, moving at least a portion of the second support structure from a first pose to a second pose, the movement of the second support structure creating kinetic energy. The method can further include transferring the kinetic energy from the second support structure to a mechanical energy transmission device, the mechanical energy transmission device converting the kinetic energy to mechanical work.

BRIEF DESCRIPTION OF THE DRAWINGS

So that the manner in which the above recited features of the present disclosure can be understood in detail, a more particular description of the disclosure, briefly summarized above, can be had by reference to the embodiments, some of which are illustrated in the appended drawings. It is to be noted, however, that the appended drawings illustrate only typical embodiments of this disclosure and are therefore not to be considered limiting of its scope. The disclosure can admit to other equally effective embodiments.

FIGS. 3A-3B are illustrations of a translating kinetic cell using translational mechanics in a passive state and an active state, according to one embodiment.

FIGS. 4A-4B are illustrations of a rotational kinetic cell using translational mechanics in a passive state and an active state, according to another embodiment.

To facilitate understanding, identical reference numeral have been used, wherever possible, to designate identical elements that are common to the Figures. Additionally, elements of one embodiment can be advantageously adapted for utilization in other embodiments described herein.

DETAILED DESCRIPTION

Figure 1A:
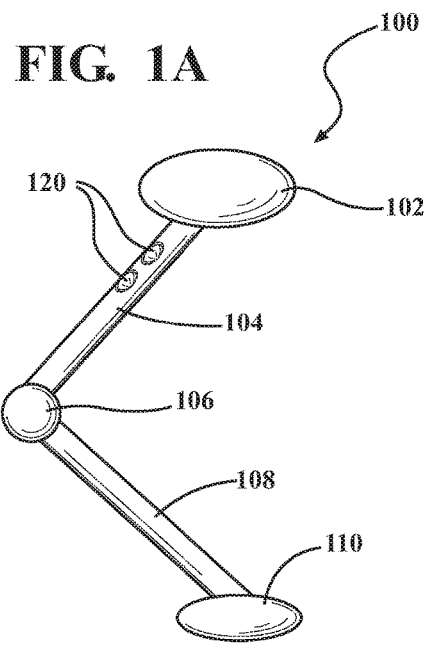
FIGS. 1A-1B are illustrations of a translational ion-responsive protein, according to one or more embodiments.

Embodiments described herein relate to the direct conversion of chemical energy into mechanical energy. Chemomechanical-inducible proteins, such as ion-responsive proteins, can be positioned in an array. The chemomechanical-inducible proteins can undergo a conformational shift when ions are directed towards it. As part of a mechanical system, this conformational shift can be directly converted to mechanical work, without electrical conversion. This conformational shift can be reversible by lowering ion concentrations or displacing the ions from binding sites.

In one embodiment, the system can have an "anode" and a "cathode" in an aqueous environment, designed to accommodate a flow of ions from one to the other. The system can further have a synthetic or biologically derived membrane, which can be disposed parallel to the direction of ion flow. Transmembrane or peripheral membrane proteins that are kinetically responsive to the ion flow can be incorporated in the membrane. In some embodiments, when ions move in bulk in one direction, the proteins can move in a coordinated fashion; and when the ions move in bulk in an opposite direction, the proteins can move in an opposite coordinated fashion. The proteins can have a strongly non-neutral pH in their aqueous region, such that movement results from ionic attraction/repulsion. A power input can be used to make the process reversible, in some examples.

In another embodiment, protein movement can be caused by presence/absence of ions, rather than by an asymmetric ion distribution in the aqueous medium. In this example, a redox center (which can be analogous to the "anode") could release ions uniformly into the aqueous medium. The protein in this version could be selected to have an allosteric site that binds the ion, resulting in protein movement. A power source can be used to cause the redox center to resorb the ions (i.e., reversibility). The ion-responsive proteins, in one embodiment, could potentially include ion sensor proteins (such as neuronal synaptic proteins), ion channels, or any other membrane protein having an allosteric ion response. Such proteins can be ion-dependent and thus must be matched to an appropriate redox center. In one example, the aqueous portions of the proteins can be tethered to a movable support structure, such as a sliding glass plate. The support structure can then be connected to external movable elements. Multiple such "kinetic cells" could be combined to increase the kinetic force generated, analogous to a battery stack as described with regard to electrochemical batteries.

In another embodiment, protein can be affixed to a support structure or membrane, and rotation or other movement of the protein in response to ion presence or concentration changes can exert a torque on the support structure, the membrane or portions thereof. For example, a "discharge" could result in protein exerted torque on a membrane, causing the support structure to rotate to a second position, which is a certain number of degrees in one direction. Reversal of the ion flow, displacement of the ions from binding site or other regeneration methods can then cause the support structure to rotate back to its starting position or a third position different from either the start position or the second position. Elements of the embodiments disclosed herein are more clearly described with relation to the figures below.

Figure 1B:
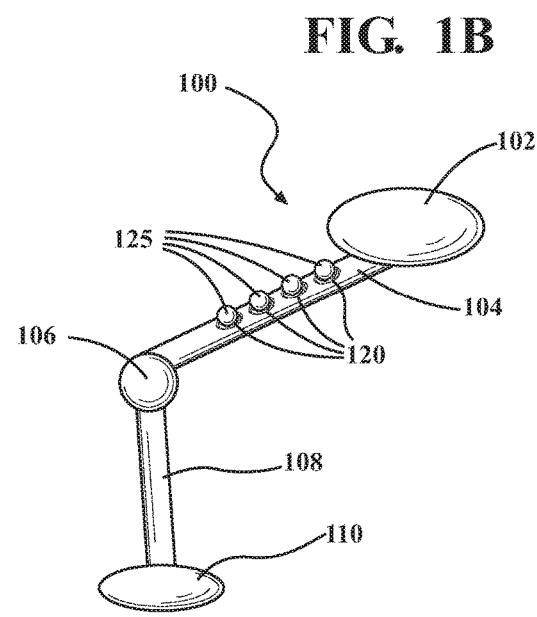

FIGS. 1A and 1B provide an illustration of an exemplary ion-responsive protein 100 using a translational conformational shift, according to embodiments described herein. Ion-responsive protein 100 shown here is illustrated using primary shapes to indicate specific active components involved in the embodiments described herein. Portions of ion-responsive protein 100 have been omitted for clarity. It will be understood by those skilled in the art that the primary, secondary and tertiary structures of a number of ion-responsive proteins, including the examples provided herein, contain numerous regions and domains which can be involved in or provide for the function described here. For sake of clarity, the primary structure, secondary structure and tertiary structure of a protein are defined as commonly understood in the art. The primary structure is the sequence of amino acids that make up a polypeptide chain. The secondary structure refers to regular, repeated patterns of folding of the protein backbone. The tertiary structure refers to the overall folding of the entire polypeptide chain into a specific 3D shape. The protein consists of, at least, all three of these structures, acting in conjunction, to perform a function.

In this embodiment, the ion-responsive protein 100 is responsive to ions or ion gradients by flexing or extending using movement at a central pivot. The ion-responsive protein 100 can include a first connection region 102, a first transmission arm 104, optionally, a joint 106, a second transmission arm 108 and a second connection region 110. The ion-responsive protein 100 undergoes a conformational shift which causes a translational movement in at least a portion of the ion-responsive protein 100.

The conformational shift in this instance, described in the sense of six degrees of freedom, involves changing translation without regard to rotation of the ion-responsive protein 100 to achieve a mechanical result (hereafter referred to as "translational mechanics"). The six degrees of freedom, as used here, are defined as movement and rotation in relation to a three-dimensional plane. Described with reference to a single object having a known starting position and direction, movement backwards and forwards (referred to as "surge"), left or right (referred to as "sway"), and up or down (referred to as "heave"), corresponds to movement on Z, X and Y planes respectively. Yaw is rotation about the Y plane. Pitch is rotation about the X plane. Roll is rotation about the Z plane.

As used herein, a conformational shift is a change in the shape of a macromolecule, such as a protein, often induced by environmental factors. A macromolecule is usually flexible and dynamic. It can change its shape in response to changes in its environment or other factors. Each possible shape is called a conformation, and a transition between them is called a conformational shift. Factors that can induce such shifts include temperature, pH, voltage, ion concentration, phosphorylation, the binding of a ligand or combinations thereof.

The first connection region 102 is the uppermost exposed region of the ion-responsive protein 100, as depicted in the illustration. The first connection region 102 can correspond with the n-terminus of the protein, the c-terminus of the protein, a specific domain as defined in the secondary or tertiary structure of the protein, or combinations thereof. The first connection region 102 can include a string of amino acids which are not essential to ion-response of the ion-responsive protein. In one embodiment, the first connection region 102 proximate the c-terminal end of the protein, with a relatively flat tertiary structure.

The first connection region 102 can be designed to connect permanently or temporarily adhere to a first structure. In a permanent adherence embodiment, the first connection region forms a permanent connection with a silanized binding site. Silanization is the covering of a surface with organofunctional alkoxysilane molecules (also referred to as "silanizing agents"). Mineral components, like glass and metal oxide surfaces, can all be silanized, as they contain hydroxyl groups which attack and displace the alkoxy groups on the silane. Displacement of the alkoxy groups leads to the forming of a covalent —Si—O—Si— bond. The organofunctional alkoxysilanes have an alkoxy group, usually the methoxy (—OCH$_3$) and the ethoxy (—OCH$_2$CH$_3$) groups. The organofunctional alkoxysilanes can be classified according to their organic functions, including aminosilanes, glycidoxysilanes, and mercaptosilanes. Exemplary aminosilanes (where the organic function is a primary or secondary amine) include APTES (3-aminopropyl)-triethoxysilane, APDEMS (3-aminopropyl)-diethoxymethylsilane, APDMES (3-aminopropyl)-dimethyl-ethoxysilane, and APTMS (3-aminopropyl)-trimethoxysilane. Exemplary glycidoxysilanes (where the organic function is an epoxide) include GPMES (3-glycidoxypropyl)-dimethyl-ethoxysilane. Exemplary Mercaptosilanes (where the organic function is a thiol) include MPTMS (3-mercaptopropyl)-trimethoxysilane, and MPDMS (3-mercaptopropyl)-methyl-dimethoxysilane.

In a temporary adherence embodiment, the first connection region 102 undergoes a conformational shift in the presence of an ion. The conformational shift of the ion-responsive protein 100 is depicted in FIG. 1B. The conformational shift of the first connection region 102 alters the tertiary structure, allowing the first connection region 102 to adhere to a contact point. The tertiary structure can be altered local to the first connection region 102 or the conformational shift can affect a larger part of the ion-responsive protein 100, up to affecting the entire protein. In this example, the first connection region 102 can detach once the ion concentration is reduced. The temporary connection with the first connection region can be mediated by a different ion than creates the translational conformational shift.

The first connection region 102 is connected to a first transmission arm 104. The first transmission arm 104 can be part of the same polypeptide chain, with a different secondary and/or tertiary structure. The first transmission arm 104 can allow for the transmission of force from a location of conformational shift. In one embodiment, the first transmission arm 104 is a relatively rigid body. The first transmission arm 104 receives the translational movement of the conformational shift, shown as a translation from a first position to a second position in FIG. 1B which it then delivers to the first connection region 102.

The embodiment shown here includes the optional component, the joint 106. In this embodiment, the first transmission arm 104 is connected with the joint 106. The joint 106 can be a region of the ion-responsive protein 100 where a majority of the conformational shift occurs. The joint 106 can be seen as a flexible connection point between the first transmission arm 104 and the second transmission arm 108. The joint 106 can be part of the same polypeptide chain as the first transmission arm 104, the second transmission arm 108 or both. The joint 106 can be comprised of multiple overlapping portions of polypeptide chain, thus strengthening the joint 106 against movement related damage.

The joint 106 can be connected to a second transmission arm 108. The second transmission arm 108 can be part of the same polypeptide chain as the joint 106 or the first transmission arm 104, a different polypeptide chain joined by disulfide bonds, a different polypeptide chain joined by the secondary or tertiary structure, or combinations thereof. The second transmission arm 108 can allow for the transmission of force from a location of conformational shift or be part of the conformational shift. In one embodiment, the second transmission arm 108 is a relatively rigid body. The second transmission arm 108 can then create the translational movement through tertiary rotations, bends or other movements of the conformational shift, which it then delivers through the joint 106 to the first transmission arm 104.

The first transmission arm 104, the joint 106, the second transmission arm 108, or combinations thereof, can have one or more ion binding sites 120. For example, the ion-responsive protein 100 is shown in FIG. 1B with the ion binding sites 120 bound by a plurality of ions 125. The ion binding sites 120 can be allosteric sites which can affect the tertiary structure of the protein. The ions delivered to the ion-responsive protein 100 can then occupy the ion binding sites 120 and create said shift. The ions 125 can act as an agonist, partial agonist or antagonist to affect the conformational shift. In one example, the ions bind creating the conformational shift (i.e., the ion binding directly creates the conformational shift). In another example, the ions bind and displace a second ion leading to the conformational shift (i.e., the shift occurs in the absence of the second ion occupying the site).

The conformational shift can be gradual or it can occur all at once. Further, the conformational shift can be ion concentration dependent or it can be affected by a single ion binding. Further, the conformational shift can be reversible when the ions are withdrawn. In this embodiment, the ion-responsive protein undergoes a second conformational shift to return to the original state once the ion concentration falls below a certain predetermined level. In this way, the conformational shift can be used multiple times to achieve the same or a cumulative mechanical work result.

The second connection region 110 is connected to a second transmission arm 108. The second connection region 110 is the lowermost region of the ion-responsive protein 100, based on the depiction in the illustration. The second connection region 110 can correspond with the n-terminus of the protein, the c-terminus of the protein, a specific domain as defined in the secondary or tertiary structure of the protein, or combinations thereof. The second connection region 110 can include a string of amino acids which are not essential to ion-response of the ion-responsive protein 100.

In one embodiment, the second connection region 110 is proximate the n-terminal end of the protein, with a relatively flat tertiary structure.

The second connection region 110 can be designed to connect permanently or temporarily adhere to a second structure, similar to the description with reference to the first connection region 102. Temporary binding and permanent binding to the second structure can be modulated in a similar fashion as described with reference to the first connection region 102. The connection to the first structure and the second structure provides the ion-responsive protein 100 the ability to deliver force to both structures simultaneously. Either structure (e.g., the first structure or the second structure) can move in response to the translational force, creating movement.

One example of ion-responsive protein 100 with movement involving a central pivot is myosin. Myosin is a highly conserved protein throughout the animal kingdom, and acts as a motor protein, in conjunction with actin, to create muscle movement. Myosin molecules are composed of a head (e.g., the first connection region 102), neck (e.g., the first transmission arm 104), and tail (e.g., the second transmission arm 108 and the second connection region 110) domain. The joint 106 is formed between the neck and tail regions. The head domain binds the filamentous actin, and uses ATP hydrolysis to generate force, in response to calcium ion concentration, and to "walk" along the filament towards the barbed (+) end. The neck domain acts as a linker and as a lever arm for transducing force generated by the catalytic motor domain, as the catalytic motor domain undergoes a conformational shift. The tail domain generally mediates interaction with cargo molecules and/or other myosin subunits. In some cases, the tail domain can play a role in regulating motor activity.

Another example of an ion-responsive protein 100 as described above is the mechanosensitive large channel protein (MscL). MscL is a homopentameric protein which governs nonselective ion transport in response to mechanical stress in E. coli. This protein, derived from E. coli, responds in the organism by undergoing a conformational shift in response to a specific pressure to create a gate to release osmotic pressure. In one embodiment, the MscL protein can have a mild substitution of the glycine, at residue 22, with a cysteine (G22C). The G22C substitution allows the gate to respond to negatively or positively charged ions by opening the gate. This conformational shift can then be converted to mechanical motion by positioning the gate on the side, such that the opening action creates a translational force. Numerous other proteins, not expressly listed here, can be used in embodiments described herein to provide translational force. In some examples, a zinc finger, having a $Ca^+$ binding domain from troponin C, is fused to a second protein of choice.

Figure 2A:
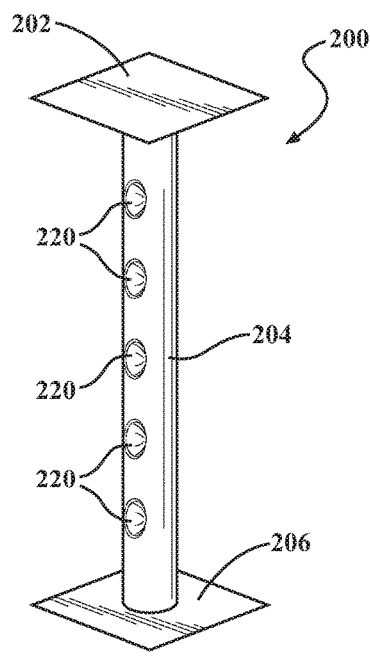
FIGS. 2A-2B are illustrations of a rotational ion-responsive protein, according to one or more embodiments.
Figure 2B:
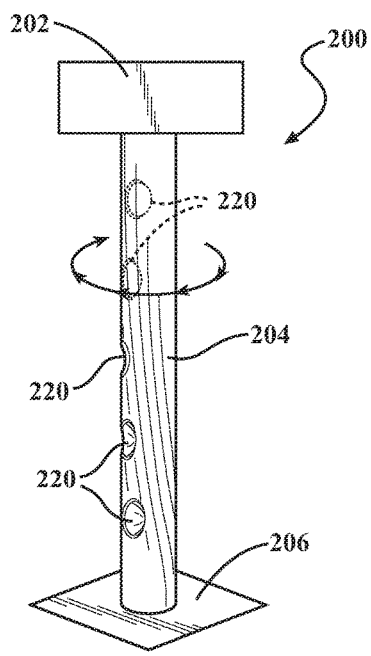

FIGS. 2A and 2B provide an illustration of an exemplary ion-responsive protein 200 using a rotational conformational shift, according to embodiments described herein. Ion-responsive protein 200 shown here is illustrated using primary shapes to indicate specific active components involved in the embodiments described herein. Portions of ion-responsive protein 200 have been omitted for clarity. It will be understood by those skilled in the art that the primary, secondary and tertiary structures of a number of ion-responsive proteins, including the examples provided herein, contain numerous regions and domains which can be involved in or provide for the function described here.

In this embodiment, the ion-responsive protein 200 is responsive to ions or ion gradients by rotating about one of the three perpendicular axes (e.g., yaw, pitch and roll). The ion-responsive protein 200 can include a first connection region 202, a first transmission region 204, and a second connection region 206. The ion-responsive protein 200 undergoes a conformational shift leading to the rotation of at least a portion of the ion-responsive protein, which can be transmitted to perform mechanical work.

The conformational shift in this instance, described in the sense of 6 degrees of freedom, involves changing rotation without regard to translation of the ion-responsive protein 200 to achieve a mechanical result (hereafter referred to as "rotational mechanics"). As used here, a conformational shift is substantially similar to the conformational shift described with reference to FIGS. 1A and 1B. Factors that can induce such shifts include temperature, pH, voltage, ion concentration, phosphorylation, the binding of a ligand or combinations thereof.

The first connection region 202 is depicted in the illustration as the uppermost exposed region of the ion-responsive protein 200. The first connection region 202 can correspond with the n-terminus of the protein, the c-terminus of the protein, a specific domain as defined in the secondary or tertiary structure of the protein, or combinations thereof. The first connection region 202 can include a string of amino acids which are not essential to ion-response of the ion-responsive protein 200. In one embodiment, the first connection region 202 proximate the c-terminal end of the protein, with a relatively flat tertiary structure.

The first connection region 202 can be designed to connect permanently or temporarily adhere to a first structure, as described with reference to FIG. 1A and FIG. 1B. In a temporary adherence embodiment, the first connection region 202 can undergo a conformational shift in the presence of an ion. The conformational shift of the ion-responsive protein 200 is depicted in FIG. 2B. The conformational shift of the first connection region 202 alters the tertiary structure, allowing the first connection region 202 to adhere to a contact point. The tertiary structure can be altered local to the first connection region 202 or the conformational shift can affect a larger part of the ion-responsive protein 200, up to affecting the entire protein. In this example, the first connection region 202 can detach once the ion concentration is reduced. The temporary connection with the first connection region can be mediated by a different ion than creates the translational conformational shift. In one embodiment, a conformational shift to achieve the mechanical work includes more than one stage. In an example, the first connection region 202 undergoes a first ion-mediated conformational shift, which exposes one or more structures or epitopes in the protein. Once the structures or epitopes are available, a second ion-mediated conformational shift can occur which creates the translational or rotational movement.

The first connection region 202 is connected to a first transmission region 204. The first transmission region 204 can be part of the same polypeptide chain, with a different secondary and/or tertiary structure. The first transmission region 204 can allow for the transmission of force from a location of conformational shift, which can occur within the first transmission region 204. In one embodiment, the first transmission region 204 is a relatively rigid body. The first transmission region 204 receives the rotational movement of the conformational shift, shown as a rotation from a first position in FIG. 2A to a second position in FIG. 2B which it then delivers to the first connection region 202.

The first transmission region 204 can have one or more ion binding sites 220. For example, the ion-responsive protein 200 is shown in FIG. 2B with the ion binding sites 220 bound by a plurality of ions 225. The ion binding sites 220 can be allosteric sites which can affect the tertiary structure of the protein, which can include causing or mediating a conformational shift. The ions delivered to the ion-responsive protein 200 can then occupy the ion binding sites 220 and create said shift. The ions 225 can act as an agonist, partial agonist or antagonist to affect the conformational shift. In one example, the ions 225 bind creating the conformational shift (i.e., the ion binding directly creates the conformational shift). In another example, the ions bind and displace a second ion leading to the conformational shift (i.e., the shift occurs in the absence of the second ion occupying the site).

The conformational shift, as mediated by the ion binding sites 220, can be gradual or it can occur all at once. Further, the conformational shift can be ion concentration dependent or it can be affected by a single ion binding at one or more of the ion binding sites 220. In one example, the ion concentration must be high enough to overcome steric hindrance to binding before the conformational shift occurs. In another example, the conformational shift can be reversible when the ions are withdrawn. In this embodiment, the ion-responsive protein undergoes a second conformational shift to return to the original state once the ion concentration falls below a certain predetermined level. In another example, the conformational shift can be continuous when the ions are withdrawn. In this embodiment, the ion-responsive protein undergoes a second conformational shift to return to the original state once the ion concentration falls below a certain predetermined level. In this way, the conformational shift can be used multiple times to achieve the same or a cumulative mechanical work result.

The second connection region 206 is connected to the first transmission region 204. The second connection region 206 is the lowermost region of the ion-responsive protein 200, based on the depiction in the illustration. The second connection region 206 can correspond with the n-terminus of the protein, the c-terminus of the protein, a specific domain as defined in the secondary or tertiary structure of the protein, or combinations thereof. The second connection region 206 can include a string of amino acids which are not essential to ion-response of the ion-responsive protein 200. In one embodiment, the second connection region 210 is proximate the n-terminal end of the protein, with a relatively flat tertiary structure.

The second connection region 206 can be designed to connect permanently or temporarily adhere to a second structure, similar to the description with reference to the first connection region 202. Temporary binding and permanent binding to the second structure can be modulated in a similar fashion as described with reference to the first connection region 202. The connection to the first structure and the second structure provides the ion-responsive protein 200 the ability to deliver force to both structures simultaneously. Either structure (e.g., the first structure or the second structure) can move in response to the translational force, creating movement.

One example of ion-responsive protein 200 with movement involving a rotation is a pentameric flagellar protein complex of PomA, PomB, MotX, MotY, and FliG. PomA, PomB, MotX, and MotY, form the polar flagellar motor of *Vibrio alginolyticus*, which functions by using an electrochemical gradient of sodium ions to drive flagellar rotation. PomA and PomB are homologous to MotA and MotB and contain four and one transmembrane segments, respectively. Both MotX and MotY have a putative single transmembrane segment. PomA and PomB functionally interact with each other in a molar stoichiometric ratio of 2 PomA:1 PomB and together form a sodium-conducting channel. To generate torque, the MotA/MotB stator unit changes its conformation in response to the sodium ion influx, and interacts with the rotor protein FliG.

Though the conformational shift of ion-responsive protein 100 or ion-responsive protein 200 are generally described with reference to movement on the X and Z planes, mechanical movement derived from the conformational shifts described herein are not limited as such. Mechanical movements and related conformational shift movements can include rotation or translation about any axis or combination of axes or in any direction. In one embodiment, a rotational ion-responsive protein can deliver pitch rotational force. In another embodiment, a translational ion-responsive protein can deliver heave translational force. Further, a translational conformational shift in one direction or a rotational conformational shift about one axis can lead to mechanical movement which is translational, rotational or combinations thereof. Further, the mechanical movement can be about any axis or in any plane, regardless the plane or axis of the conformational shift.

As described above, the conformational shifts can be used as part of devices, systems and methods described herein. The conformational shift of the protein or protein complex in question is a direct conversion of chemical energy to mechanical energy. By positioning the proteins such that the conformational shifts are delivered directionally and as a group, the force created by the conformational shift can be multiplied and utilized to perform mechanical work.

FIGS. 3A and 3B are illustrations of a translating kinetic cell 300 using translational mechanics in a passive state and an active state, according to one embodiment. The kinetic cell 300 can include a donor source 302, a recipient source 304, a chamber 306, an array of proteins 308, a membrane 309, an ion-containing solution 310, a support structure 312 and a membrane holding assembly 314. The term "kinetic cell" as used herein refers to a single unit of components, including an array of proteins, capable of converting chemical energy directly to mechanical energy. The kinetic cell is described as a single unit because the kinetic cell can be modularized to act in conjunction with other kinetic cells toward the same mechanical work (e.g., three kinetic cells connected in series to deliver force to a single motor).

The donor source 302 is the source of a target ion, either cations or anions, which are used for activation of the proteins for the kinetic cell 300. The target ion is the ion which the ion-responsive protein is responsive to. The donor source 302 can provide one or more ion types, such as $Ca^{2+}$ ions or $Na^+$ ions. Thus, the donor source 302 can be an anode, a cathode or another source of charged particles useful for the activation of the ion-responsive proteins of the array of proteins 308. The array of proteins 308 can include ion-responsive proteins such as ion-responsive protein 100, described with reference to FIG. 1. In one embodiment, the donor source 302 is a source of charged particles, where the ions produced include $Ca^{2+}$. The donor source 302 can be a uniform material, such as a block of a calcium salt. The donor source 302 can be further modified to increase solubility, such as by pore formation. The donor source 302 delivers ions to the ion-containing solution 310 at a controllable rate.

The recipient source 304 receives the cation or anions delivered to the ion-containing solution 310. Thus, the recipient source 304 can be an anode, a cathode or another recipient of charged particles after use in the activation of the ion-responsive proteins 100 of the array of proteins 308. In one embodiment, the recipient source 304 is a recipient of charged particles producing $Ca^{2+}$. The recipient source 304 can be a uniform material, such as a material which binds $Ca^{2+}$ ions in solution. In one example, the recipient source 304 is a citrate source. The recipient source 304 can be further modified to increase solubility, such as by pore formation. The recipient source 304 receives ions or otherwise binds ions in the ion-containing solution 310, to either maintain a steady state level of the ions or to reduce ion concentrations. In one embodiment, the recipient source 304 can be used as an off switch for the kinetic cell 300.

The chamber 306 is an enclosure positioned around the internal components of the kinetic cell. The chamber 306, which can also be referred to as an enclosure, forms a liquid tight region around the components of the kinetic cell 300. The chamber 306 can be made of electrically non-conductive material. In some embodiments, the chamber 306 comprises multiple layers, thus creating an outer chamber and one or more inner chambers, which can create a barrier to leakage. Typical materials that can be employed for this purpose include the synthetic plastics, such as polymethyl-methacrylate, copolymeric acrylonitrile methylstyrene, copolymeric acrylonitrile styrene, high-density nylon and high-density polyethylene.

The array of proteins 308 is an organized region of ion-responsive proteins, such as ion-responsive protein 100 or the ion-responsive protein 200. The proteins in the array of proteins 308 are organized and positioned such that they can deliver force with a high degree of synchrony. This allows for conversion of the force from the conformational shift to useful mechanical work. The array of proteins can consist of proteins of a variety of mechanical types, such as translational ion-responsive proteins, rotational ion-responsive proteins, ion-responsive proteins which both translate and rotate, or combinations thereof.

The array of proteins 308 can be affixed or otherwise connected to the membrane 309. In this way, the array of proteins 308 can deliver force from the conformational shift in a specific and calculated direction. The array of proteins 308 can be positioned in a uniform direction or they can non-uniformly, such that the delivery of force from the conformational shift acts substantially in unison to achieve a specific mechanical work function. As shown here, the array of proteins 308 is positioned uniformly in a set of seven rows. In this example, the array of proteins 308 are positioned such that the conformational shift creates a movement or shift to the right, as seen from the plane of the illustration.

The array of proteins 308, as affixed or connected, can be a uniform type of ion-responsive protein/protein complex or it can be a combination of two or more different types of ion-responsive proteins/protein complexes. As shown in this example, each protein of the array of proteins 308 are the same type of translational ion-responsive protein. In further embodiments, the proteins of the array of proteins 308 can be an individually alternating combination of two or more types of translational ion-responsive protein. In another embodiment, the proteins of the array of proteins 308 can be an alternating combination, by row and/or column, of two or more types of translational ion-responsive protein. Further combinations or permutations of the above are contemplated herein and will be understood by those skilled in the art.

The array of proteins 308, as shown here, has 133 proteins forming the array. However, this quantity of proteins is for exemplary purposes only and can include substantially more proteins to achieve the translational force desired. In one embodiment, the array of proteins 308 can include greater than one thousand (1000) proteins, such as one million proteins. Larger quantities of proteins in the array of proteins 308 can be used with embodiments described herein.

The membrane 309 can be made from a material which is substantially impermeable to the electrolyte and the ions to which the array of proteins 308 respond, such as polyethylene or Teflon plastic. The membrane 309 can be mounted in and positioned by a membrane holding assembly 314. The membrane holding assembly 314 can be a device capable of securely holding an end of the membrane 309, such as two mating annular elements. The membrane holding assembly 314 can be positioned between the donor source 302 and the recipient source 304 so that the membrane 309 is stretched between the two. The membrane 309 can further define a solution-membrane space in the chamber 306. The solution-membrane space, the membrane 309 and the array of proteins 308 is in communication with the ion-containing solution 310. The membrane 309 can further include one or more binding sites, where the array of proteins can be affixed.

The ion-containing solution 310 is a solution-containing energy sources and ions necessary for the conformational shift of the ion-responsive proteins. The ion-containing solution 310 immerses the array of proteins 308, such that the polypeptide chain of each of the proteins receives limited exposure to the atmosphere. Further, the ion-containing solution 310 can be in fluid communication with the membrane 309, the donor source 302, and the recipient source 304. The ion-containing solution 310 can be largely free of ions which affect the ion-responsive protein, when ions are not being delivered by the donor source 302. The ion-containing solution 310 can contain one or more protein stabilizing reagents to protect the proteins from deterioration, denaturation or cleavage by proteases. Protein stabilization reagents can include glycerol, protease inhibitors (e.g., phenylmethylsulfonyl fluoride [PMSF], 4-benzenesulfonyl fluoride hydrochloride [AEBSF], pepstatin, leupeptin, aprotinin, ethylenediaminetetraacetic acid [EDTA], and benzamidine), sodium azide, 2-Isopropyl-5-methylphenol (IPMP), and others. Flow rate and circulation of the ion-containing solution 310 can be controlled, such that the kinetic cell 300 can be maintained at a steady rate and changes to the ion concentration are received quickly by the array of proteins 308.

The support structure 312 is one of many types of connection region for conversion of force to mechanical energy. The support structure 312 can be made from a rigid material, such as glass, plastics, metals, ceramics, or others. The support structure 312 can include a conductive or non-conductive materials. Further, the support structure 312 can be composed of more than one material, which can provide benefits in stability and adhesion. In one embodiment, the support structure 312 is composed of a fiberglass mesh. The support structure 312 can be designed to be light weight. Further, the support structure 312 can include friction-reducing devices, such as lubricating strips, rollers, ball bearing or others, to reduce loss of mechanical energy during a mechanical process. The support structure 312 can be shaped such that the chamber 306 is at least partially sealed. In one embodiment, the support structure 312 is a rectangular shape, designed to fit over and partially seal.

In one example, the array of proteins 308 are affixed to the support structure 312 using a silanizing agent, as described above. The support structure 312 would have at least one surface treated with one or more silanizing agents. The treated regions would bind to the silanizing agent, creating organic sites through a Si—O—Si bond. The exposed organic groups of the support structure 312 can then be affixed to the array of proteins 308 by UV crosslinking. In another embodiment, the array of proteins 308 can be affixed to the silanized support structure 312 using a crosslinking reagent, such as sulfosuccinimidyl 6-[3'-(2-pyridyldithio) propionamido] hexanoate (Sulfo-LC-SPDP), succinimidyl 6-[3'-(2-pyridyldithio)-propionamido]hexanoate (LC-SPDP), or N-succinimidyl 3-(2-pyridyldithio) propionate.

In operation, using the embodiment shown in FIGS. 3A and 3B, the donor source 302 of the kinetic cell 300 is placed in contact with the ion-containing solution 310, or otherwise activated, such that ions are delivered to the ion-containing solution 310. Ions are then delivered through the ion-containing solution 310 to the array of proteins 308. The flow rate of the ion-containing solution 310 over the array of proteins 308 can be controlled to deliver ions at an appropriate rate for creating the conformational shift but at a rate lower than would damage or otherwise affect the function of the array of proteins 308. In some embodiments, the flow rate is controlled simply by the diffusion of ions into the ion-containing solution from an anode (e.g., the donor source 302) and a cathode (e.g., the recipient source 304).

The ions then bind, flow through or otherwise affect the ion-responsive proteins of the array of proteins 308 to create a conformational shift, as shown in FIG. 3B. The conformational shift of the array of proteins 308, shown in FIGS. 3A and 3B, as connected to the membrane 309, creates a translational force in a unified direction. The translational force is then transferred from the array of proteins 308 to the connected support structure 312. Upon receiving the translational force, the support structure slides from a first position shown in FIG. 3A to a second position in FIG. 3B. Thus, the support structure 312 allows the cumulative force of the array of proteins 308 to be delivered to a mechanical system for further use.

As proteins are sensitive to changes in the environment, the kinetic cells (the kinetic cell 300, the kinetic cell 400, the kinetic cell 500, or combinations thereof) can be temperature and pH controlled during and after operation. In one embodiment, the kinetic cells can be maintained at a pH between about 7.0 and about 7.5, such as from about 7.25 to about 7.45. In another embodiment, the temperature can be maintained at or below about 37 degrees Celsius, such as at or below about 25 degrees Celsius, at or below about 4 degrees Celsius, or others. In another embodiment, salinity of the kinetic cell can be controlled using phosphate buffered saline (PBS). In a further embodiment, the kinetic cells may include chaperone proteins. Chaperone proteins are proteins which interact with other proteins and help them to reach their final, active conformation. Chaperone proteins do this by binding the other proteins in an unfolded or partially folded state and subsequently releasing them in an altered form. Chaperone proteins which may be used in embodiments described herein can include the heat-shock protein (hsp) family (e.g., hsp60, hsp70, hsp90, etc.), GroEL protein proteins, GroES (a co-chaperone protein), TCP1 protein family, or others.

Figure 4B:
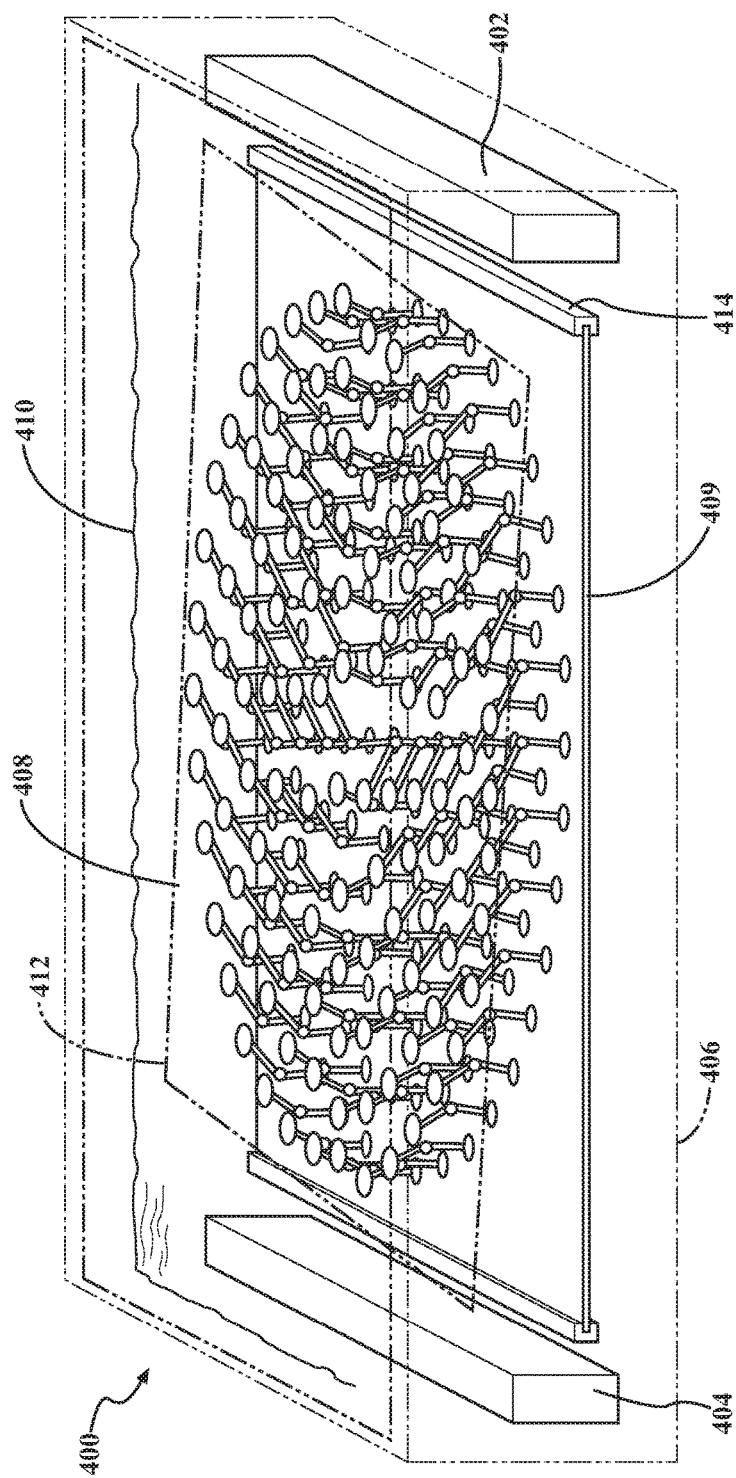

FIGS. 4A and 4B are illustrations of a translating kinetic cell 400 using rotational mechanics in a passive state and an active state, according to one embodiment. The kinetic cell 400 can include a donor source 402, a recipient source 404, a chamber 406, an array of proteins 408, a membrane 409, an ion-containing solution 410, a support structure 412 and a membrane holding assembly 414. The kinetic cell described here uses a translational motion to create a rotational effect, which can be harnessed for mechanical work as described herein.

The donor source 402 is the source of either cations or anions which are used for activation of the proteins for the kinetic cell 400. The donor source 402 can provide one or more ion types, such as $Ca^{2+}$ and $Na^+$ ions. Thus, the donor source 402 can be an anode, a cathode or another source of charged particles useful for the activation of the ion-responsive proteins 100 of the array of proteins 408. In one embodiment, the donor source 402 is a source of charged particles, where the ions produced include $Ca^{2+}$. The donor source 402 can be a uniform material, such as a block of a calcium salt. The donor source 402 can be further modified to increase solubility, such as by pore formation. The donor source 402 delivers ions to the ion-containing solution 410 at a controllable rate.

The recipient source 404 receives the cation or anions delivered to the ion-containing solution 410. The recipient source 404 can be substantially similar to the recipient source 304, described with reference to FIGS. 3A and 3B. Thus, the recipient source 404 can be an anode, a cathode or another recipient of charged particles after use in the activation of the ion-responsive proteins 100 of the array of proteins 408. In one embodiment, the recipient source 404 is a recipient of charged particles producing $Ca^{2+}$. The recipient source 404 can be a uniform material, such as sodium persulfate. In another example, the recipient source 404 is a citrate source. The recipient source 404 can be further modified to increase solubility, such as by pore formation. The recipient source 404 receives ions or otherwise binds ions in the ion-containing solution 410, to either maintain a steady state level of the ions or to reduce ion concentrations. In one embodiment, the recipient source 404 can be used as an off switch for the kinetic cell 400.

The chamber 406 is an enclosure positioned around the internal components of the kinetic cell. The chamber 406 can be substantially similar to the chamber 306, described with reference to FIGS. 3A and 3B. The chamber 406, which can also be referred to as an enclosure, forms a liquid tight region around the components of the kinetic cell 400. The chamber 406 can be made of electrically non-conductive material. In some embodiments, the chamber 406 comprises multiple layers, thus creating an outer chamber and one or more inner chambers, which can create a barrier to leakage.

The array of proteins 408 is an organized region of ion-responsive proteins, such as ion-responsive protein 100 or the ion-responsive protein 200. The array of proteins 408 can be substantially similar to the array of proteins 308, described with reference to FIGS. 3A and 3B. The proteins in the array of proteins 408 are organized and positioned such that they can deliver force with a high degree of synchrony. This allows for conversion of the force from the conformational shift to useful mechanical work. The array of proteins 408 can consist of proteins of a variety of mechanical types, such as translational ion-responsive proteins, rotational ion-responsive proteins, ion-responsive proteins which both translate and rotate, or combinations thereof. The array of proteins 408, as affixed or connected, can be a uniform type of ion-responsive protein/protein complex or it can be a combination of two or more different types of ion-responsive proteins/protein complexes. As shown in this example, each protein of the array of proteins 408 are the same type of translational ion-responsive protein.

The array of proteins 408 can be affixed or otherwise connected to the membrane 409. In this way, the array of proteins 408 can deliver force from the conformational shift in a specific and calculated direction. The array of proteins 408 can be positioned in a uniform direction or they can non-uniformly, such that the delivery of force from the conformational shift acts substantially in unison to achieve a specific mechanical work function. As shown here, the array of proteins 408 is positioned as slightly rotated in the yaw direction with a center of rotation in the center of the membrane 409 to deliver force tangentially and rotationally. The array of proteins 408 are positioned such that the conformational shift creates a rotational movement or shift about the central axis, as seen from the plane of the illustration.

The membrane 409 forms a limited movement structure, which resists the movement of the conformational shift in the array of proteins 408. The membrane described here can be substantially similar to the membrane 309 described with reference to FIGS. 3A and 3B. The membrane 409 can be mounted in and positioned by a membrane holding assembly 414. The membrane holding assembly 414 can be positioned between the donor source 402 and the recipient source 404 so that the membrane 409 is stretched between the two. The membrane 409 can further define a solution-membrane space in the chamber 406. The solution-membrane space, the membrane 409 and the array of proteins 408 is in communication with the ion-containing solution 410. The membrane 409 can further include one or more binding sites, where the array of proteins 408 can be affixed.

The ion-containing solution 410 is a solution-containing energy sources and ions necessary for the conformational shift of the ion-responsive proteins. The ion-containing solution 310 can be substantially similar to the ion-containing solution 310, described with reference to FIGS. 3A and 3B. The ion-containing solution 410 can be in fluid communication with the membrane 409, the donor source 402, and the recipient source 404. Flow rate and circulation of the ion-containing solution 410 can be controlled, such that the kinetic cell 400 can be maintained at a steady rate and changes to the ion concentration are received quickly by the array of proteins 408.

The support structure 412 is one of many types of connection region for conversion of force to mechanical energy. The support structure 412 can be substantially similar to the support structure 312, described with reference to FIGS. 3A and 3B. The support structure 412 can be made from a rigid material. The support structure 412 can include a conductive or non-conductive materials. Further, the support structure 412 can be composed of more than one material, which can provide benefits in stability and adhesion. The support structure 412 can be designed to be light weight. Further, the support structure 412 can include friction-reducing devices, as described with reference to support structure 312 of FIGS. 3A and 3B. The support structure 412 can be shaped such that the chamber 406 is at least partially sealed. In one embodiment, the support structure 412 is a rectangular shape, designed to fit over and partially seal the chamber 406.

In one example, the array of proteins 408 are affixed to the support structure 412 using a silanizing agent, as described above. The treatment with a silanizing agent and crosslinking of proteins is substantially similar to that which is described with reference to the support structure 312 of FIGS. 3A and 3B.

In operation, using the embodiment shown in FIGS. 4A and 4B, the donor source 402 of the kinetic cell 400 is placed in contact with the ion-containing solution 410, or otherwise activated, such that ions are delivered to the ion-containing solution 410. Ions are then delivered through the ion-containing solution 410 to the array of proteins 408. The flow rate of the ion-containing solution 410 over the array of proteins 408 can be controlled to deliver ions at an appropriate rate for creating the conformational shift but at a rate lower than would damage or otherwise affect the function of the array of proteins 408. In some embodiments, the flow rate is controlled simply by the diffusion of ions into the ion-containing solution from an anode (e.g., the donor source 402) and a cathode (e.g., the recipient source 404).

The ions then bind, flow through or otherwise affect the ion-responsive proteins of the array of proteins 408 to create a conformational shift, as shown in FIG. 4B. The conformational shift of the array of proteins 408, shown in FIGS. 4A and 4B, as connected to the membrane 409, creates a translational force about the central axis, with each protein applying force in a tangential direction to the axis. The translational force is then transferred from the array of proteins 408 to the connected support structure 412. Upon receiving the translational force, the support structure rotates from a first position shown in FIG. 4A to a second position in FIG. 4B. Thus, the support structure 412 allows the cumulative force of the array of proteins 408 to be delivered to a mechanical system for further use.

Figure 5A:
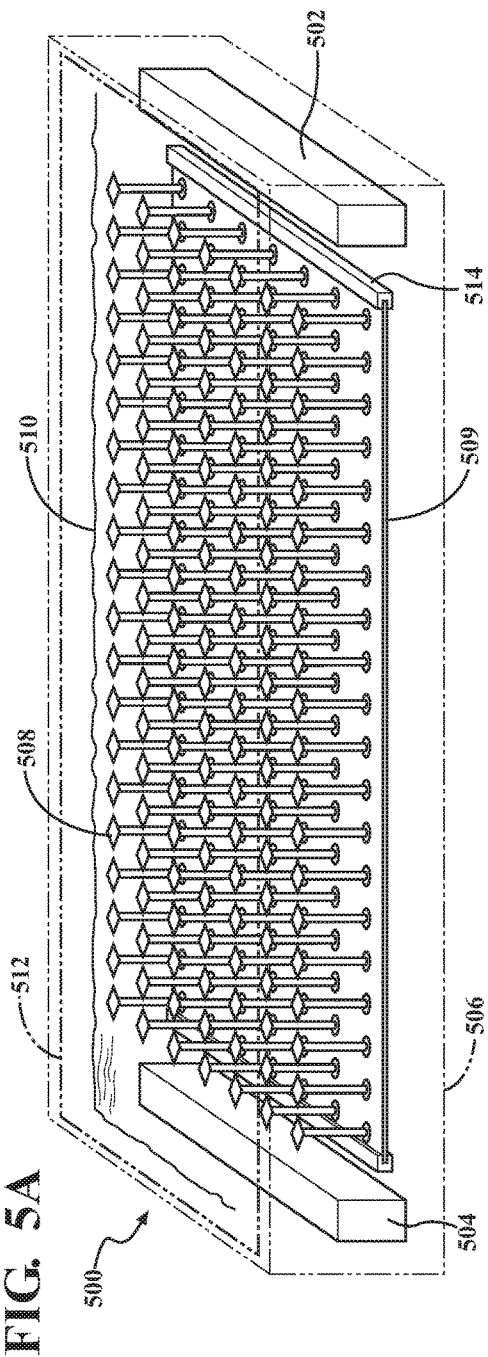
FIGS. 5A-5B are illustrations of a rotational kinetic cell using rotational mechanics in a passive state and an active state, according to another embodiment.
Figure 5B:
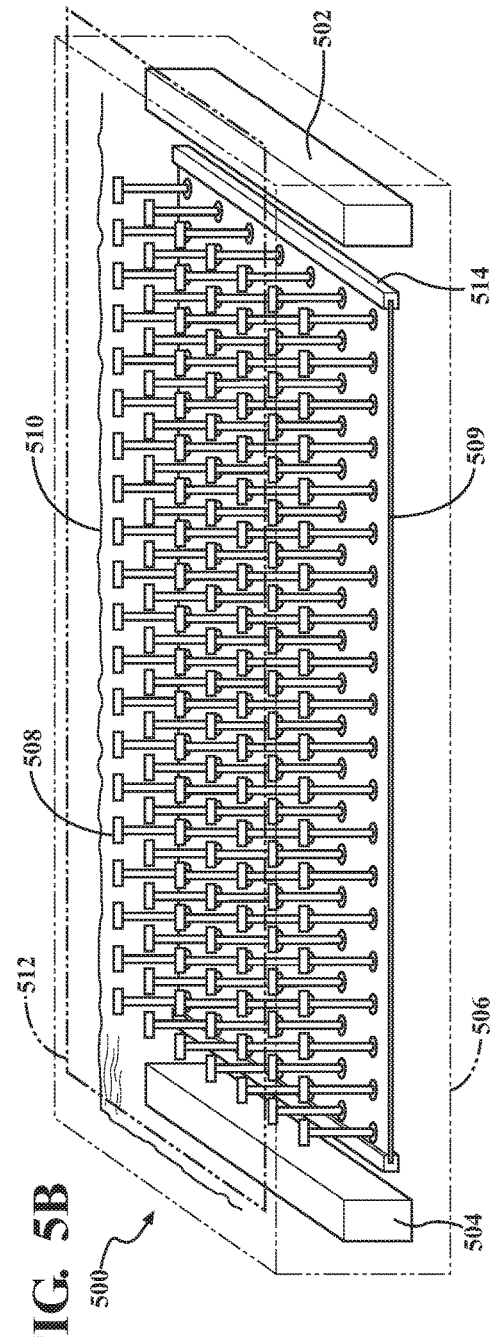

FIGS. 5A and 5B are illustrations of a rotating kinetic cell 500 using rotational mechanics in a passive state and an active state, according to one embodiment. The kinetic cell 500 can include a donor source 502, a recipient source 504, a chamber 506, an array of proteins 508, a membrane 509, an ion-containing solution 510, a support structure 512 and a membrane holding assembly 514. The kinetic cell described here uses a rotational motion to create a rotational effect, which can be harnessed for mechanical work as described herein.

The donor source 502 is the source of either cations or anions which are used for activation of the proteins for the kinetic cell 500. The donor source 502 can provide one or more ion types, such as $Ca^{2+}$ and $Na^+$ ions. Thus, the donor source 502 can be an anode, a cathode or another source of charged particles useful for the activation of the ion-responsive proteins 100 of the array of proteins 508. In one embodiment, the donor source 502 is a source of charged particles, where the ions produced include $Na^+$. The donor source 502 can be a uniform material, such as a sodium ion source. The donor source 502 can be further modified to increase solubility, such as by pore formation. The donor source 502 delivers ions to the ion-containing solution 510 at a controllable rate.

The recipient source 504 receives the cation or anions delivered to the ion-containing solution 510. The recipient source 504 can be substantially similar to the recipient source 304, described with reference to FIGS. 3A and 3B. Thus, the recipient source 504 can be an anode, a cathode or another recipient of charged particles after use in the activation of the ion-responsive proteins 100 of the array of proteins 508. In one embodiment, the recipient source 504 is a recipient of charged particles producing $Na^+$. The recipient source 504 can be a uniform material, such as sodium persulfate. In another example, the recipient source 504 is a citrate source. The recipient source 504 can be further modified to increase solubility, such as by pore formation. The recipient source 504 receives ions or otherwise binds ions in the ion-containing solution 510, to either maintain a steady state level of the ions or to reduce ion concentrations. In one embodiment, the recipient source 504 can be used as an off switch for the kinetic cell 500.

The chamber 506 is an enclosure positioned around the internal components of the kinetic cell. The chamber 506 can be substantially similar to the chamber 306, described with reference to FIGS. 3A and 3B. The chamber 506, which can also be referred to as an enclosure, forms a liquid tight region around the components of the kinetic cell 500. The chamber 506 can be made of electrically non-conductive material. In some embodiments, the chamber 506 comprises multiple layers, thus creating an outer chamber and one or more inner chambers, which can create a barrier to leakage.

The array of proteins 508 is an organized region of ion-responsive proteins, such as the ion-responsive protein 200 described with reference to FIG. 2. The proteins in the array of proteins 508 are organized and positioned such that they can deliver force with a high degree of synchrony. This allows for conversion of the force from the conformational shift to useful mechanical work. The array of proteins 508 can consist of rotational ion-responsive proteins, ion-responsive proteins which both translate and rotate, or combinations thereof. The array of proteins 508, as affixed or connected, can be a uniform type of ion-responsive protein/protein complex or it can be a combination of two or more different types of ion-responsive proteins/protein complexes. As shown in this example, each protein of the array of proteins 508 are the same type of rotational ion-responsive protein, such as the pentameric flagellar protein complex described with reference to FIG. 2.

The array of proteins 508 can be affixed or otherwise connected to the membrane 509 such that the protein creates a pore through the membrane 509. In this way, the array of proteins 508 can deliver rotational force from the conformational shift in a specific and calculated direction. The array of proteins 508 can be positioned in a uniform direction, such that the delivery of force from the conformational shift acts substantially in unison to achieve a specific mechanical work function. As shown here, the array of proteins 508 is positioned in a uniform manner across the membrane 509 to deliver force rotationally. The array of proteins 508 are positioned such that the conformational shift creates a rotational movement or shift about the center axis of each protein in the array of proteins 508.

The array of proteins 508 may include proteins which allow for a partial rotation or a full rotation. Some proteins which can be used as part of the array of proteins 508, create a reversible rotational conformational shift (hereinafter "partial rotation"). In this embodiment, the partial rotation is due to a rotation based on shifted conformation within the protein, such that a twist or other structural tension is formed. Once the inducer of the conformational shift is removed, the protein is relaxed, reverting back from the shifted conformation to either an initial conformation or an altered conformation. The optional second conformation is different from either the initial conformation or the shifted conformation, and is the result of undergoing a conformational shift and not having an internal mechanism to return to the initial conformation. Some proteins which can be used as part of the array of proteins 508, create an irreversible rotational conformational shift (hereinafter "full rotation"). In this embodiment, the full rotation is due to a rotation based on shifted conformation within a protein complex, such that a one or more proteins move with relation to another protein without creating structural tension. Once the inducer of the conformational shift is removed, the protein is relaxed, and the protein reverts back from the shifted conformation to an initial conformation. However, in the full rotation embodiment, the conformational shift to the initial conformation doesn't change the position of the protein in the protein complex. The full rotation embodiment can then enter the shifted conformation again and again moving between all possible positions within the complex and creating full rotations in the process. The full rotation embodiment can be unidirectional.

The membrane 509 forms a limited movement structure, which resists the movement of the conformational shift in the array of proteins 508. The membrane described here can be substantially similar to the membrane 309 described with reference to FIGS. 3A and 3B. The membrane 509 can be mounted in and positioned by a membrane holding assembly 514. The membrane and the membrane holding assembly for an impermeable barrier, such that communication between an upper region 520 and a lower region 522 The membrane holding assembly 514 can be positioned between the donor source 502 and the recipient source 504 so that the membrane 509 is stretched between the two. The membrane 509 can further define a solution-membrane space in the chamber 506. The solution-membrane space, the membrane 509 and the array of proteins 508 is in communication with the ion-containing solution 510. The membrane 509 can further include one or more binding sites, where the array of proteins 508 can be affixed.

The ion-containing solution 510 is a solution-containing energy sources and ions necessary for the conformational shift of the ion-responsive proteins. The ion-containing solution 310 can be substantially similar to the ion-containing solution 310, described with reference to FIGS. 3A and 3B. The ion-containing solution 510 can be in fluid communication with the membrane 509, the donor source 502, and the recipient source 504. Flow rate and circulation of the ion-containing solution 510 can be controlled, such that the kinetic cell 500 can be maintained at a steady rate and changes to the ion concentration are received quickly by the array of proteins 508.

Figure 5C:
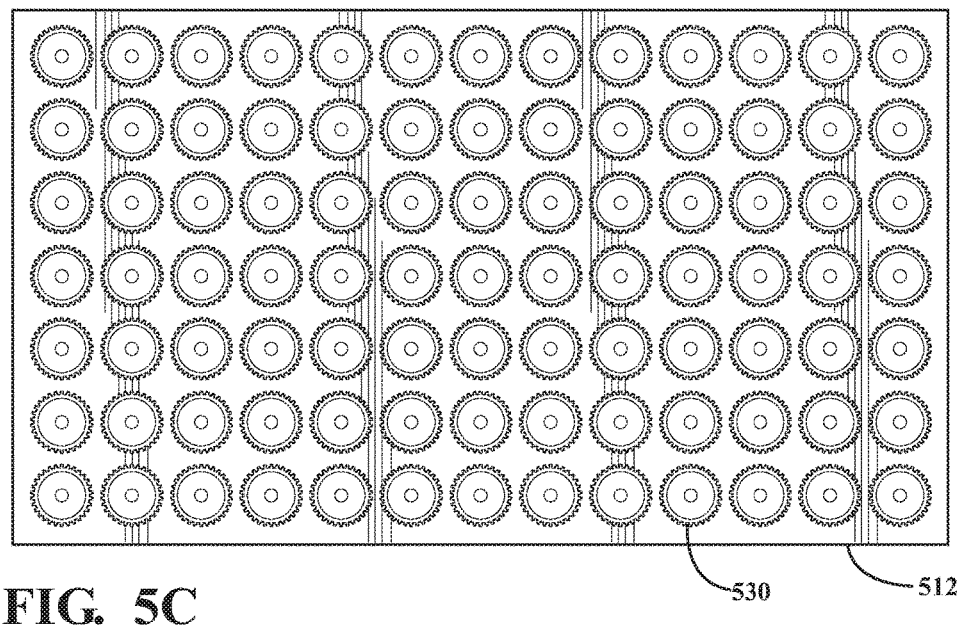
FIG. 5C is an illustration of a support structure having a plurality of rotational supports, according to one embodiment.

The support structure 512, shown in greater detail in FIG. 5C, is a further embodiment for conversion of force to mechanical energy when using rotational conformational shifts. The support structure 512 can be made from a rigid material, such as glass, plastics, metals, ceramics, or others. The support structure 512 can include a conductive or non-conductive materials. Further, the support structure 512 can be composed of more than one material, which can provide benefits in stability and adhesion. In one embodiment, the support structure 512 is composed of a ceramic material. The support structure 512 can be designed to be light weight. Further, the support structure 512 can include friction-reducing devices, such as lubricating strips, rollers, ball bearing or others, to reduce loss of mechanical energy during a mechanical process. The support structure 512 can be shaped such that the chamber 506 is at least partially sealed. In one embodiment, the support structure 312 is a rectangular shape, designed to fit over and partially seal.

Embedded in the support structure 512 can be a number of rotational supports 530. The rotational supports 530 can be a device to deliver rotational force through one or more mechanical movements, such as a gear, a wheel, or a spring. The rotational supports 530 can be configured to match the positioning and quantity of proteins in the array of proteins 508. The rotational supports 530 can further be selectively treated with a silanizing agent, such that the rotational supports 530 are the only available binding sites for the proteins of the array of proteins 508. In one example, the array of proteins 508 are affixed to the support structure 512 using a silanizing agent, as described above. The treatment with a silanizing agent and crosslinking of proteins is substantially similar to that which is described with reference to the support structure 312 of FIGS. 3A and 3B. The rotational supports 530 can be configured to rotate independent of one another or in an interconnected fashion.

In operation, using the embodiment shown in FIGS. 5A and 5B, the donor source 502 of the kinetic cell 500 is placed in contact with the ion-containing solution 510, or otherwise activated, such that ions are delivered to the ion-containing solution 510. Ions are then delivered through the ion-containing solution 510 to the array of proteins 508. The flow rate of the ion-containing solution 510 over the array of proteins 508 can be controlled to deliver ions at an appropriate rate for creating the conformational shift but at a rate lower than would damage or otherwise affect the function of the array of proteins 508. In some embodiments, the flow rate is controlled simply by the diffusion of ions into the ion-containing solution from an anode (e.g., the donor source 502) and a cathode (e.g., the recipient source 504).

The ions then channeled through the pores created by the ion-responsive proteins of the array of proteins 508 through the membrane 509, to create a conformational shift, as shown in FIG. 5B. As shown, the ions are channeled through the array of proteins 508, from the upper region 520 to the lower region 522. The conformational shift of the array of proteins 508, shown in FIGS. 5A and 5B, as connected to the membrane 509, creates a rotational force about the central axis of each individual protein, with each protein applying force rotationally to an attached rotational support 530. The rotational force is then transferred from the array of proteins 508 to the rotational supports 530 of the connected support structure 512. Upon receiving the rotational force, the rotational support 530 rotates from a first position to a second position, with the rotation of the array of proteins shown in FIG. 5A and in FIG. 5B. Thus, the support structure 512 allows the cumulative rotational force of the array of proteins 508 to be delivered to a rotational mechanical system for further use.

The illustrations of FIGS. 3A-5C depict three embodiments of the chemomechanical devices, such as kinetic cells. Specifically, chemomechanical cells as part of a translational force to translational mechanical work embodiment, a translational force to rotational mechanical work embodiment, and a rotational force to rotational mechanical work embodiment, are depicted. These embodiments are intended as exemplary embodiments and should not be considered limiting of possible embodiments, which are specifically contemplated herein. In another example, a chemomechanical cell can provide a rotational force to translational mechanical work embodiment. In a further example, a chemomechanical cell can provide a rotational and a translational force to translational mechanical work embodiment. In a further example, a chemomechanical cell can provide a rotational and a translational force to rotational and translational mechanical work embodiment. The wide variety of permutations of the embodiments described herein will be understood by those skilled in the art.

In further embodiments, the chemomechanical devices of FIGS. 3A-5C can perform mechanical work using translational force or rotational force generated in multiple directions. In one embodiment, the array of proteins can create a force at least two directions by undergoing sequential or reversible conformational shifts. In these embodiment, the chemomechanical devices can convert this to an effectively unidirectional force by inducing a macroscopic 180 degree rotation of the kinetic cell around an axis orthogonal to the direction of the force. In a rotational force embodiment, the kinetic cell begins at a first pose. A first ion flow then creates a conformational shift in the array of proteins, which causes the protein to rotate clockwise about a rotational axis. The kinetic cell can then rotate 180 degrees about an axis orthogonal to the rotational axis. Then, a second ion flow, such as a different ion or a change in concentration, can be delivered to the proteins leading to a second conformational shift in the protein. Now, in this case, the second conformational shift is counterclockwise about the rotational axis as compared to the original pose of the kinetic cell. However, the second conformational shift is clockwise about the rotational axis as compared to the second pose. By shifting the pose of the kinetic cell, multiple directional translational force or rotational force can be translated to mechanical work from the same kinetic cell.

Figure 6:
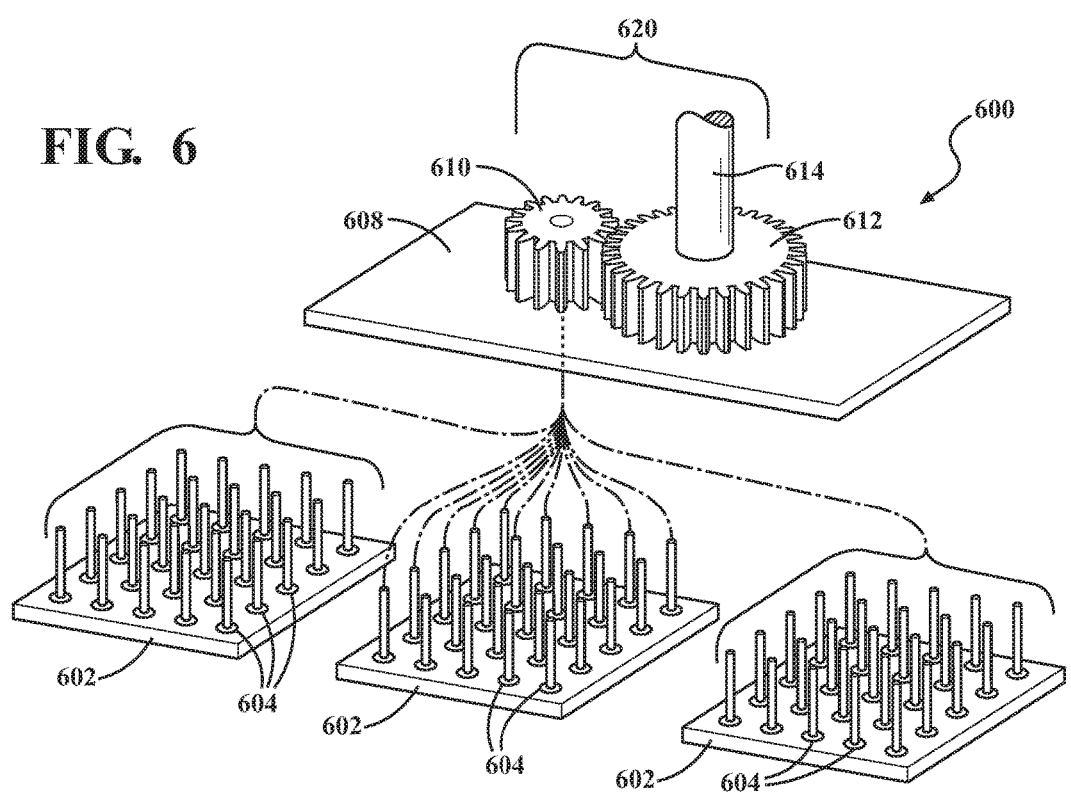
FIG. 6 is an illustration of a chemomechanical system, according to one embodiment.

FIG. 6 depicts a chemomechanical system 600 for converting chemical energy to mechanical movement. The chemomechanical system 600 can include one or more kinetic cells 602, each kinetic cell 602 having a plurality of rotational supports 604, a connection end 606 and a mechanical energy transmission device 608 in communication with the connection end 606. The mechanical energy transmission device 608 can include a force conversion device 620, depicted here as including a first gear 610, a second gear 612 and a transmission rod 614. The chemomechanical system 600 produces force using the one or more kinetic cells 602, as described in the embodiments above. The mechanical energy transmission device 608 is configured, through the force conversion device 620, to receive movement from the connection end; convert said movement to a first force; and apply said first force to perform mechanical work.

The chemomechanical system 600 begins with force provided by the kinetic cells, as described above. Each of the one or more kinetic cells 602 can include a chamber, a donor source, a recipient source, a membrane; an array of proteins; an ion-containing solution; and a support structure. All elements of the one or more kinetic cells 602 can be substantially similar to the kinetic cell 300, kinetic cell 400, the kinetic cell 500 or combinations thereof, described with reference to FIGS. 3A, 4A and 5A respectively. Shown here, the one or more kinetic cells 602 are rotational ion-responsive embodiments. The one or more kinetic cells 602 may include proteins which allow for a partial rotation or a full rotation, as described with reference to FIG. 5B. In this example, the one or more kinetic cells provide for a full rotation.

The one or more kinetic cells 602 can each have a plurality of rotational supports 604. The plurality of rotational supports 604 can be substantially similar to the rotational supports 530, described with reference to FIG. 5A-5C. Shown here are three kinetic cells 602, each having twenty-five (25) rotational supports 604. In practice, there can be substantially more rotational supports 604 than shown here, such as thousands or millions of rotational supports 604. The plurality of rotational supports 604 can be connected to the respective ion-responsive proteins in the kinetic cells 602, thus rotating the rotational supports 604 in a first direction.

The plurality of rotational supports 604 then transfer that rotation to the mechanical energy transmission device 608 through the connection end 606. The connection end 606 is a device for transmission of the force from the kinetic cell 602. The connection end 606 can be used to accumulate the force created by one or more kinetic cells 602 into a single output force. In this embodiment, the connection end 606 is a series of cables which are connected to the plurality of rotational supports 604. The connection end 606 is in communication with the force conversion device 620.

The force conversion device 620 is a series of mechanical devices which, as part of the system, convert the force delivered to the connection end 606 to mechanical work. The force conversion device 620 is generally configured to receive movement from the connection end 606; convert said movement to a first force, and apply said first force to perform mechanical work. The embodiment described herein describes an exemplary system for conversion of rotational force from one or more kinetic cells 602 to rotational mechanical work. However, this is not intended to be limiting, as the disclosure lends itself to further embodiments. In another example, the force conversion device 620 can convert rotational force from one or more kinetic cells 602 to translational mechanical work, using a system of cables and pulleys. In another example, the force conversion device 620 can convert translational force from one or more kinetic cells 602 to translational mechanical work, using a system of cables, ratchet mechanisms and a sliding rail device. One skilled in the art will understand the breadth of this disclosure in light of the variety of mechanical systems which can be employed beneficially with embodiments disclosed herein.

The force conversion device 620 is configured to receive movement from the connection end 606 (i.e., force delivered from the one or more kinetic cells 602). In this embodiment, the force conversion device 620 is a series of gears, including the first gear 610, the second gear 612 and the transmission rod 614. The first gear 610, depicted here as a single gear, receives the force from the connection end 606. Though depicted with one first gear 610, the force conversion device can have numerous gears allowing for independent transmission of force to the force conversion device 620. The first gear 610 is in communication with the second gear 612.

The force conversion device 620 is then configured to convert said movement to a first force. In this embodiment, either the first gear 610 or the second gear 612 can be used for collection of the first force from the force applied by the one or more kinetic cells 602. In this embodiment, the first gear 610 receives the rotational force from the one or more kinetic cell 602. The first gear, in this embodiment, accumulates the force from the one or more kinetic cells 602. In another embodiment, the second gear 612 can receive force from one or more first gears 610, thus accumulating the first force in place of the first gear 610 as shown here. Further combinations of multiple first gears 610 and multiple second gears 612 are contemplated without specific recitation herein.

The first force can then be delivered to the second gear 612 of the force conversion device 620. The second gear 612 can be larger or smaller than the first gear 610, which can be used to control speed of rotation, inertia and other factors of the conversion. The second gear 612 can be positioned and designed to mate with the first gear 610, such that the first gear 610 and the second gear 612 do not slip or grind during rotation.

The force conversion device 620 can be configured to apply said first force to perform mechanical work. In this embodiment, the second gear 612 rotates transmission rod 614. The transmission rod 614 will be understood by one skilled in the art as a connection to a mechanical device, either large such as heavy machinery used in industrial production or small such as a wheel in a remote controlled car. As the second gear 612 transmits the first force to the transmission rod 614, the transmission rod 614 delivers that first force to the mechanical device to perform mechanical work. There are a variety of permutations of mechanical devices which are specifically contemplated and can be beneficially incorporated into embodiments disclosed herein, without further recitation.

Figure 7:
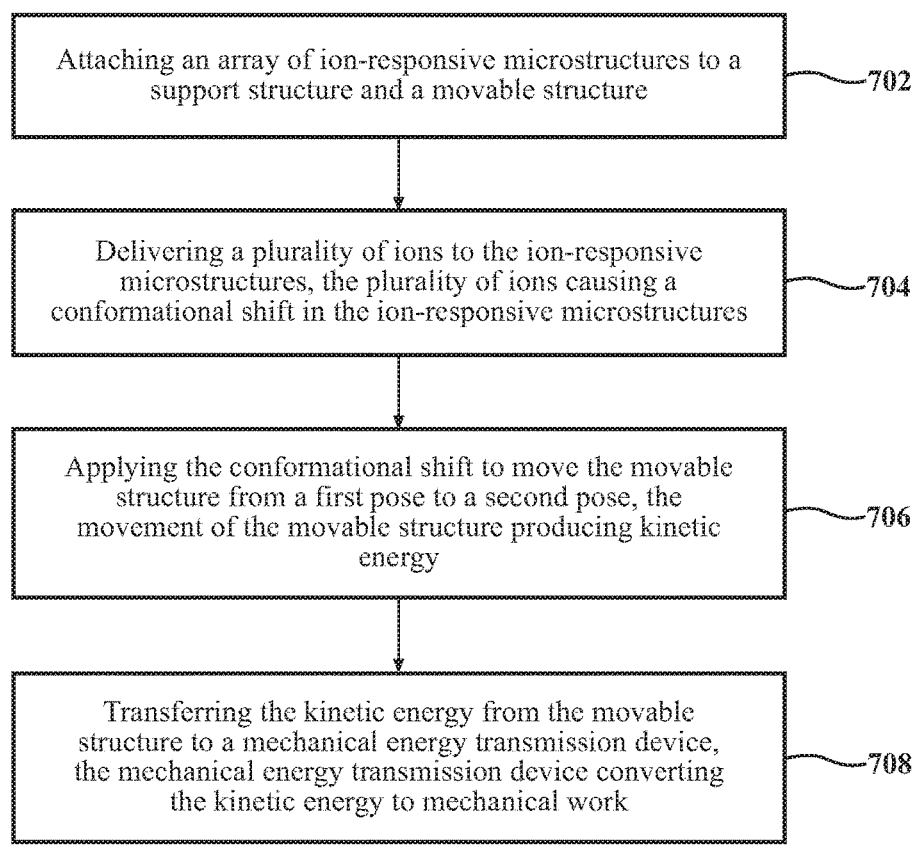
FIG. 7 is a flow diagram of a method of converting chemical energy to mechanical energy, according to embodiments described herein.

FIG. 7 discloses a flow diagram of a method 700 for converting chemical energy to mechanical energy. The method 700 includes attaching an array of ion-responsive microstructures to a first support structure and a second support structure, at 702; delivering a plurality of ions to the ion-responsive microstructures, the plurality of ions causing a conformational shift in the ion-responsive microstructures, at 704; applying the conformational shift create a movement in the second support structure, moving at least a portion of the second support structure from a first pose to a second pose, the movement of the second support structure producing kinetic energy, at 706; and transferring the kinetic energy from the second support structure to a mechanical energy transmission device, the mechanical energy transmission device converting the kinetic energy to mechanical work, at 708.

The method 700 begins with attaching an array of ion-responsive microstructures to a first support structure and a second support structure, at 702. The array of ion-responsive microstructure can include ion-responsive proteins, ion-responsive compounds (such as ion-responsive polymers), or other ion-responsive structure. "Microstructure", as used herein, refers to structures which occur on the micro scale or smaller, such as proteins, other chemical compounds, nanorobotics, or others. The ion-responsive microstructures can be positioned in an array, as described above. When using ion-responsive proteins as the ion-responsive microstructures, the array of proteins can be substantially similar to the array of proteins, described with reference to FIGS. 3A-5C.

A plurality of ions are then delivered to the ion-responsive microstructures, at 704. The plurality of ions can be delivered at a controlled concentration over the ion-responsive microstructures. In further embodiments, the plurality of ions can be delivered to an active site on the ion-responsive structures. The plurality of ion can cause a conformational shift in the ion-responsive microstructures. The shift in conformation can be delivered translationally or rotationally, described with reference to FIGS. 3A-5C. The shift in conformation may be a change in tertiary structure, as in ion-responsive proteins. In further embodiments, the conformational shift can be a change in secondary structure, in the case of ion-responsive polymers. Ion-responsive polymers include polymers which respond with a conformational shift to changes in ion concentration, such as Sodium alginate (which is responsive to $Ca^{2+}$) or Chitosan (which is responsive to $Mg^{2+}$). Chitosan is a linear polysaccharide composed of randomly distributed $\beta$-(1→4)-linked D-glucosamine (deacetylated unit) and N-acetyl-D-glucosamine (acetylated unit).

The conformational shift is then applied create a movement in the second support structure, moving at least a portion of the second support structure from a first pose to a second pose, at 706. The first support structure is a structure, which is connected with the proteins, and controls the delivery of force during the conformational shift. The first support structure allows conformational shift of the ion-responsive microstructures to be converted to mechanical work. Pose, as used in the art, is intended to mean any change in position or orientation. As such, the conformational shift can be delivered to the first support structure to move the second support structure from a first position to a second position. In another embodiment, components of the first support structure move without changing the position of the majority of the first support structure, an example of which is described with reference to FIG. 5C. The movement of the first support structure produces kinetic energy. The kinetic energy at the first support structure can be in the form of a translation or a rotation in part or all of the first support structure.

The kinetic energy is then transferred from the second support structure to a mechanical energy transmission device, at 708. The mechanical energy transmission device, is a device configured to receive the kinetic energy from the first support structure; convert said kinetic energy to a first force; and apply said first force to perform mechanical work. The mechanical energy transmission device converts the kinetic energy to mechanical work. The kinetic energy can be delivered to the mechanical energy transmission device through a connection end, described above with reference to FIG. 6. The connection end then delivered the kinetic energy as translation force, rotational force or both. The force is accumulated and delivered to a mechanical system to perform mechanical work.

The flowcharts and block diagrams in the figures illustrate the architecture, functionality, and operation of possible embodiments of systems, methods and computer program products according to various embodiments. In this regard, each block in the flowcharts or block diagrams may represent a module, segment, or portion of code, which comprises one or more executable instructions for implementing the specified logical function(s). It should also be noted that, in some alternative embodiments, the functions noted in the block may occur out of the order noted in the Figures. For example, two blocks shown in succession may, in fact, be executed substantially concurrently, or the blocks may sometimes be executed in the reverse order, depending upon the functionality involved.

The systems, components and/or methods described above can be realized in hardware or a combination of hardware and software and can be realized in a centralized fashion in one processing system or in a distributed fashion where different elements are spread across several interconnected processing systems. Any kind of processing system or other apparatus adapted for carrying out the methods described herein is suited. A typical combination of hardware and software can be a processing system with computer-usable program code that, when being loaded and executed, controls the processing system such that it carries out the methods described herein. The systems, components and/or methods also can be embedded in a computer-readable storage, such as a computer program product or other data programs storage device, readable by a machine, tangibly embodying a program of instructions executable by the machine to perform methods and methods described herein. These elements also can be embedded in an application product which comprises all the features enabling the embodiment of the methods described herein and, which when loaded in a processing system, is able to carry out these methods.

The terms "a" and "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The phrase "at least one of . . . and . . . " as used herein refers to and encompasses any and all possible combinations of one or more of the associated listed items. As an example, the phrase "at least one of A, B and C" includes A only, B only, C only, or any combination thereof (e.g. AB, AC, BC or ABC).

While the foregoing is directed to embodiments of the disclosed devices, systems, and methods, other and further embodiments of the disclosed devices, systems, and methods can be devised without departing from the basic scope thereof. The scope thereof is determined by the claims that follow.

What is claimed is:

1. A kinetic cell, comprising:
    a chamber;
    a donor source comprising a target ion, the donor source in a first position in the chamber;
    a recipient source in a second position in the chamber;
    a membrane positioned in the chamber between the donor source and the recipient source;
    an array of proteins comprising a plurality of ion-responsive proteins, each ion-responsive protein having a first connecting region and a second connecting region, the ion-responsive protein being attached to the membrane at the second connecting region;
    an ion-containing solution in the chamber and in fluid communication with the donor source, the recipient source, and the array of proteins; and
    a support structure attached to at least a portion of the array of proteins at the first connecting region.

2. The kinetic cell of claim 1, wherein the ion-containing solution comprises a protein stabilizing reagent.

3. The kinetic cell of claim 1, wherein the array of proteins comprises two or more types of ion-responsive protein.

4. The kinetic cell of claim 1, wherein the array of proteins delivers a rotational force.

5. The kinetic cell of claim 1, wherein the membrane forms a barrier between an upper region and a lower region in the chamber.

6. The kinetic cell of claim 5, wherein the array of proteins forms a plurality of pores through the membrane, wherein the plurality of pores are selective for the target ion.

7. The kinetic cell of claim 1, wherein the support structure further comprises a plurality of rotational supports.

8. The kinetic cell of claim 1, wherein the second connection region is reversibly attached to the support structure.

9. A chemomechanical system for converting chemical energy to mechanical movement, comprising:
    one or more kinetic cells, each of the one or more kinetic cells comprising:
        a chamber;
        a donor source comprising a target ion, the donor source in a first position in the chamber;
        a recipient source in a second position in the chamber;
        a membrane positioned in the chamber between the donor source and the recipient source;
        an array of proteins comprising a plurality of ion-responsive proteins, each ion-responsive protein having a first connecting region and a second connecting region, the ion-responsive protein being attached to the membrane at the second connecting region;
        an ion-containing solution in the chamber and in fluid communication with the donor source, the recipient source, and the array of proteins; and
        a support structure attached to at least a portion of the array of proteins at the first connecting region, the one or more kinetic cells configured to produce a movement; and
    a mechanical energy transmission device connected with the one or more kinetic cells, the mechanical energy transmission device comprising:

a connection end forming a connection with at least a portion of the support structure, the connection end configured to receive the movement from the one or more kinetic cells; and a force conversion device connected with the connection end, the force conversion device configured to:
receive movement from the connection end;
convert said movement to a first force; and
apply said first force to perform mechanical work.

10. The chemomechanical system of claim 9, wherein the ion-containing solution comprises a protein stabilizing reagent.

11. The chemomechanical system of claim 9, wherein the array of proteins comprises a single type of ion-responsive protein.

12. The chemomechanical system of claim 9, wherein the array of proteins delivers a rotational force.

13. The chemomechanical system of claim 9, wherein the membrane forms a barrier between an upper region and a lower region in the chamber.

14. The chemomechanical system of claim 13, wherein the array of proteins forms a plurality of pores through the membrane, wherein the plurality of pores are selective for the target ion.

15. The chemomechanical system of claim 9, wherein the support structure further comprises a plurality of rotational supports.

16. The chemomechanical system of claim 15, wherein the connection end is configured to receive rotation from the plurality of rotational supports.

17. The chemomechanical system of claim 9, wherein the one or more kinetic cells are configured to be maintained at a temperature of at or less than about 37 degrees Celsius.

18. A method for converting chemical energy to mechanical energy, comprising:

attaching an array of ion-responsive microstructures to a first support structure and a second support structure;

delivering a plurality of ions to the array of ion-responsive microstructures, the plurality of ions causing a conformational shift in the ion-responsive microstructures;

directing the conformational shift to create a movement in the second support structure, moving at least a portion of the second support structure from a first pose to a second pose, the movement of the second support structure creating kinetic energy; and transferring the kinetic energy from the second support structure to a mechanical energy transmission device, the mechanical energy transmission device converting the kinetic energy to mechanical work.

19. The method of claim 18, wherein the array of ion-responsive microstructures comprises ion-responsive proteins.

20. The method of claim 18, wherein delivering the plurality of ions further comprises immersing at least a portion of the array of ion-responsive microstructures in an ion-containing solution.

* * * * *